United States Patent [19]

Suzuki et al.

[11] Patent Number: 5,795,866
[45] Date of Patent: Aug. 18, 1998

[54] ETS1 GENE: A HUMAN TUMOR SUPPRESSOR GENE

[75] Inventors: Hiroaki Suzuki, Sapporo, Japan; Narayan K. Bhat, North Potomac, Md.; Takis S. Papas, Charleston, S.C.

[73] Assignee: The United States of America as represented by the Department of Health and Human Services, Washington, D.C.

[21] Appl. No.: 854,522

[22] Filed: May 12, 1997

Related U.S. Application Data

[62] Division of Ser. No. 191,889, Feb. 4, 1994, Pat. No. 5,629,192.

[51] Int. Cl.⁶ ........................................... A61K 38/00
[52] U.S. Cl. ..................... 514/12; 514/13; 514/14; 514/15; 514/16; 514/17; 514/18; 514/19
[58] Field of Search .......................... 514/12–19

[56] References Cited

U.S. PATENT DOCUMENTS 5,629,192   5/1997   Suzuki et al. ................. 435/172.3

*Primary Examiner*—Sheela Huff
*Attorney, Agent, or Firm*—Townsend and Townsend and Crew LLP

[57] ABSTRACT

The present invention relates, in general, to methods for reducing cell tumorigenicity. More particularly, the present invention provides a method for reducing cell tumorigenicity comprising transfecting a tumor cell with an ETS1 gene, the tumor cell not endogenously expressing the ETS1 gene. In addition, the present invention provides a method for reducing cell tumorigenicity comprising contacting a tumor cell with a peptide expressed by an ETS1 gene, the tumor cell not endogenously expressing the ETS1 gene. The methods of the present invention are particularly useful for reducing tumorigenicity in epithelial tumor cells.

6 Claims, No Drawings

ETS1 GENE: A HUMAN TUMOR SUPPRESSOR GENE

This application is a divisional application of U.S. Ser. No. 08/191,889, now U.S. Pat. No. 5,629,192. This application is incorporated by reference in its entirety for all purposes.

FIELD OF THE INVENTION

The present invention relates generally to the ETS1 gene and to the ETS1 protein expressed by this gene. More particularly, the present invention relates to methods of reducing cell tumorigenicity by transfecting a tumor cell with an ETS1 gene or, by contacting a tumor cell with a peptide expressed by an ETS1 gene, the tumor cell not endogenously expressing the ETS1 gene.

BACKGROUND OF THE INVENTION

ETS1 is a member of the ets gene family which includes ETS1 and ETS2 (Watson, et al., , ERG, ELK1 and ELK2, SPi1/PU.1, Fli1, GABPα, SAP1, ELF1, PEA3 and *Drosophila melanogaster* E47. The ETS1 gene is expressed in lymphoid cells, endothelial cells, astrocytes, but not detected in normal epithelial cells. It has previously been shown that the ETS1 gene is developmentally regulated in the mouse thymus. The ETS1 gene products are expressed at high levels in resting T-cells and its expression decreases following T-cell activation. The ETS1 gene encodes a nuclear protein and is phosphorylated by $Ca^{2+}$ mediated events. It has been shown that the ets proteins bind to purine rich sequences ('GGA' core) in the promoter and enhancer region of cellular and viral genes and function as transcription factors. Among ETS family genes identified so far, only ETS1 and ETS2 have calmodulin-dependent kinase II consensus sequences, and have been shown to be phosphorylated by $Ca^{2+}$ mediated events. Thus, the ETS1 protein may be a mediator of $Ca^{2+}$ signals (generated by coupling of ligand to their cell surface receptors) into genetic reprogramming of specific set of genes involved in cellular function.

Two major isoforms of human ETS1 (i.e., p51 and p42) proteins have been identified in lymphoid cells and cell lines. p51 is encoded by full length ETS1 mRNA, while p42 is a product of alternatively spliced mRNA lacking exon VII. It has been shown that the major site of phosphorylation is in the sequences encoded by exon VII of ETS1, suggesting that p51, but not p42, may be involved in the $Ca^{2+}$ mediated signal transduction processes. Also, it has been shown that p42 ETS1 or truncated form of ETS1 binds to DNA more efficiently than the full-length ETS1 protein. Several mechanisms including intramolecular repression, or the presence of an inhibitory domain have been proposed to explain weaker binding activities of the full-length ETS1 protein. However, it is possible that the p51, but not p42, may be able to interact with other proteins to form a complex that is not capable of binding to DNA. Alternatively, the flanking sequences outside the 'GGA' core greatly influence the DNA-binding activities. The former hypothesis is strengthened by the recent demonstration that ETS1 family members are able to interact with other nuclear proteins. Sequence-specific binding of ELK1 is dependent on association with serum response factor; similarly associated GABPα with GABPβ and PU.1 with NFEMS enhances their capacity to bind DNA. However, an effort to demonstrate such a bonafide partners for ETS1 was not successful. Also, the temporal and tissue-specific expression pattern and different mode of regulation of ETS1 gene during T-cell activation suggest that ETS1 may be capable of either inducing or representing a certain set of genes. In lymphoid cells, identification of such ETS1-responsive genes is also complicated by the presence of multiple isoforms of ETS gene products lacking important functional domains, and therefore it is difficult to assign function to one or the other forms of ETS1.

To identify ETS1-responsive genes and to find out if the cellular phenotype plays any role in the ETS1 function, ETS1 has been expressed in DLD-1, a colon epithelial tumor cell line. The amounts of ETS1 expressed in transfected DLD-1 cells were comparable to those amounts expressed in lymphoid cells. The ectopically-expressed ETS1 has a relative molecular mass of 51 kDa and has an isoelectric point of 5.2. The ETS1 expressed in DLD-1 cells binds to the purine-rich motif containing 5'-CCGGAAGT-3', but not very well to the 5'-CAGGAAGT-3' (PEA3 motif), suggesting that the DNA-binding activity of ETS1 is influenced by flanking sequences outside the 'GGA' core. It was also demonstrated that (i) the DNA-binding activity of ETS1 expressed in DLD-1 cells is very similar to ETS1 expressed in lymphoid cells and does not depend on cell background; (ii) the ETS1 produced in DLD-1 cells is biologically active and is capable of inducing a 54.5 kDa polypeptide; and (iii) the ETS1-responsive 54.5 kDa polypeptide is also expressed at high levels in lymphoid cells expressing abundant levels of ETSI gene products.

Although it has been found that the tranfected DLD-1 cell line, i.e., a colon epithelial tumor cell line, exogenously expresses abundant levels of ETS1, the effect of ETS1 gene expression on cell growth and tumorigenicity has yet to be determined.

SUMMARY OF THE INVENTION

It has now been discovered that the ETS1 gene possesses tumor suppressor activity. More particularly, it has been found that introduction of the wild-type ETS1 gene into cells that do no endogenously express this gene results in tumor suppressive activity. Although tumor formation frequently results from multiple genetic alterations, expression of wild-type ETS1 can overcome these changes and suppress tumorigenicity by either blocking the downstream targets for ETS2 gene products or, by inducing new gene products required for tumor suppression.

Moreover, it has been found that the ETS1 gene is useful for reducing tumorigenicity in cells that do not endogenously express this gene. More particularly, it has been found that the ETS1 gene is useful for reducing tumorigenicity in epithelial cells as these cells do not express ETS1 endogenously. As such, the present invention provides a method for reducing cell tumorigenicity, the method comprising: transfecting a tumor cell with an ETS1 gene, the tumor cell not endogenously expressing this gene. In addition, the present invention provides a method for reducing cell tumorigenicity, the method comprising contacting a tumor cell with a peptide expressed by an ETS1 gene, the tumor cell not endogenously expressing this gene.

Other advantages, objects, features and embodiments of the present invention will become apparent from the description which follows.

DEFINITIONS

"Nucleic acid," as used herein, refers to a deoxyribonucleotide (DNA) or ribonucleotide (RNA) in either single- or double-stranded form, and unless otherwise limited, encompasses known analogs of natural nucleotides which can function in a manner similar to the naturally occurring nucleotides.

The phrase "nucleic acid sequence" refers to a single- or double-stranded polymer of deoxyribonucleotide or ribonucleotide bases read from the 5' to the 3' end. It includes both self-replicating plasmids, infectious polymers of DNA or RNA and non-functional DNA or RNA. Additionally, substantial nucleic acid sequence identity exists when a nucleic acid segment will hybridize, under selective hybridization conditions, to a complement of another nucleic acid strand. Nucleotide sizes are given in either kilobases (kb) or base pairs (bp). These are estimates derived from agarose or acrylamide gel electrophoresis.

The phrase "DNA sequence" refers to a single- or double-stranded DNA polymer composed of the nucleotide bases, adenosine, thymidine, cytosine and guanosine.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or sequences which may be introduced to provide codon preference in a specific host cell.

The term "complementary" refers to a nucleic acid segment that will hybridize, under selective hybridization conditions, to a complement of another nucleic acid strand. Selectivity of hybridization exists when hybridization occurs that is more selective than total lack of specificity. See, Kanehisa, *Nucleic Acids Res.* 12:203 (1984), incorporated herein by reference.

"Isolated" or "substantially pure," when referring to nucleic acids, refer to those that have been purified away from other cellular components and contaminants, i.e., other cellular nucleic acids and/or proteins, by standard techniques, including, for example, alkaline/SDS treatment, CsCl banding, column chromatography, and others purification techniques well known in the art. See, e.g., *Methods in Enzymology*, Vol. 152: Guide to Molecular Cloning Techniques (Berger and Kimmel (eds.), San Diego: Academic Press, Inc. (1987)), and *Current Protocols in Molecular Biology* (Ausubel, et al., (ed.), Greene Publishing and Wiley-Interscience, New York (1987)), both of which are incorporated herein by reference.

"Nucleic acid probe" refers to an oligonucleotide which binds through complementary base pairing to a subsequence of a target nucleic acid. The nucleic acid probe may be, for example, a DNA fragment prepared by amplification methods such as by PCR or it may be synthesized by either the phosphoramidite method described by Beaucage and Carruthers (*Tetrahedron Lett.* 22:1859-1862 (1981)), or by the triester method according to Matteucci, et al. (*J. Am. Chem. Soc.* 103:3185 (1981)), both of which are incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included as the complementary strand will work equally well in situations where the target is a double stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. It will be understood by those of skill that minor mismatches can be accommodated by reducing the stringency of the hybridization media. For discussions of nucleic acid probe design and annealing conditions, see, e.g., Sambrook, et al., *Molecular Cloning: A Laboratory Manual* (2nd Ed., Vols. 1-3, Cold Spring Harbor Laboratory (1989)), *Methods in Enzymology*, Vol. 152: Guide to Molecular Cloning Techniques (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), all of which are incorporated herein by reference.

The phrases "expression control sequence" or "expression control cassette" refer to nucleotide sequences which are capable of affecting expression of a structural gene in a host compatible with such sequences. Such cassettes include at least a promoter and, optionally, transcription termination signals. The term "promoter" refers to a region of DNA upstream from the structural gene and involved in the recognition and binding of a DNA polymerase and other proteins necessary to initiate transcription. Additional factors necessary or helpful in effecting expression may also be used as described herein.

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Techniques for nucleic acid manipulation, such as subcloning nucleic acid sequences encoding polypeptides into expression vectors, labelling probes, DNA hybridization, and so on are described generally, for example, in Sambrook, et al. (1989) supra., Berger and Kimmel, (1987), supra. or Ausubel, et al., (1987), supra., both of which are incorporated herein by reference. "Expression vectors," "cloning vectors" or "vectors" are often plasmids or other nucleic acid molecules that are able to replicate in a chosen host cell. Expression vectors may replicate autonomously, or they may replicate by being inserted into the genome of the host cell using methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction and in a mammalian cell for expression.

The term "plasmid" refers to an autonomous self-replicating circular DNA molecule and includes both the expression and nonexpression types. Where a recombinant microorganism or cell culture is described as hosting an "expression plasmid," this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

A "hybrid virion" is a virion comprising genome, core, and envelope components derived from more than one virus.

The term specifically includes "pseudovirions" which historically have been defined as containing the genome from one virus and the structural proteins from another.

A "packaging cell" is a genetically constructed mammalian tissue culture cell that produces the necessary viral structural proteins required for packaging. The cells are incapable of producing infectious virions until a defective genome is introduced into the cells. The genetic material for the viral structural proteins is not transferred with the virions produced by the cells, hence the virus cannot replicate.

A "replication-defective" virion or retroviral vector is one produced by a packaging cell as defined above. Such a virion infects a target cell but is incapable of producing progeny virions which can infect other cells.

"Peptides," "polypeptides" and "oligopeptides" are chains of amino acids (typically L-amino acids) whose α carbons are linked through peptide bonds formed by a condensation reaction between the carboxyl group of the α carbon of one amino acid and the amino group of the α carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free α-amino group on the amino acid at the amino terminal of the peptide or to the α-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide or to the carboxyl group of an amino acid at any other location within the peptide.

Typically, the amino acids making up a polypeptide are numbered in order, starting at the amino terminal and increasing in the direction of the carboxy terminal of the polypeptide. Thus, when one amino acid is said to "follow" another, that amino acid is positioned closer to the carboxy terminal of the polypeptide than the "preceding" amino acid.

The term "residue" as used herein refers to an amino acid or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci.* (U.S.A.), 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The percentage of sequence identity between two sequences is determined by comparing two optimally aligned sequences over a window of comparison of at least 20 positions. The percentage is calculated by determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity.

For instance, a preferred method for comparing sequences uses the GAP program based on the algorithm of Needleman, et al., supra. Typically, the default values for all parameters are selected. These are gap weight: 5.0, length weight: 0.30, average match: 1.0, and average mismatch: 0.0.

The term "substantial identity" means that a polynucleotide or polypeptide comprises a sequence that has at least 80% sequence identity, preferably 90%, more preferably 95% or more, compared to a reference sequence over a comparison window of about 20 bp to about 2000 bp, typically about 50 to about 1500 bp, usually about 350 bp to about 1200. The values of percent identity are determined using the GAP program, above. Another indication that nucleotide sequences are substantially identical is if two molecules hybridize to each other under stringent conditions.

The term "biologically active" refers to a peptide sequence that will interact with naturally occurring biological molecules to either activate or inhibit the function of those molecules in vitro or in vivo. The term "biologically active" is most commonly used herein to refer to the protein expressed by ETS1 gene that reduces or inhibits cell tumorigenicity both in vitro or in vivo.

The phrase "consisting essentially of" is used herein to exclude any elements that would substantially alter the essential properties of the VIP antagonists to which the phrase refers. Thus, the description of a polypeptide "consisting essentially of . . . " excludes any amino acid substitutions, additions, or deletions that would substantially alter the biological activity of that polypeptide.

The term "contacting" is used herein interchangeably with the following: introducing into, combined with, added to, mixed with, passed over, incubated with, injected into, flowed over, etc. Moreover, the peptides of the present invention may be "administered" by any conventional method such as, for example, parenteral, oral, topical, and inhalation routes. Moreover, the term "transfecting" is used herein to refer to the process of transfering genetic material to a cell by the addition of DNA using, fir example, a viral vector.

"An amount sufficient" or "an effective amount" is that amount of a peptide or DNA-liposome which reduces or inhibits cell tumorigenicity or, which provides either a subjective relief of a symptom(s) or an objectively identifiable improvement as noted by the clinician or other qualified observer.

As used herein, the terms "isolated," "substantially pure" and "biologically pure" are used interchangeably and describe a protein that has been separated from components which naturally accompany it. Typically, a monomeric protein is substantially pure when at least about 60% to about 75% of a sample exhibits a single polypeptide backbone. Minor variants or chemical modifications typically share the same polypeptide sequence. A substantially purified protein will typically comprise about 85% to about 90% of a protein sample, more usually about 95% and, more preferably, it will be over about 99% pure. Protein purity or homogeneity may be indicated by a number of means well known in the art, such as, for example, by polyacrylamide gel electrophoresis (PAGE) of a protein sample, followed by visualizing a single polypeptide band on a polyacrylamide gel upon staining. For certain purposes, high resolution will be needed and, thus, HPLC or other similar means can be utilized for purification in such instances.

The proteins of the present invention can be purified to substantial homogeneity by standard techniques well known in the art, including, for example, selective precipitation with such substances as ammonium sulfate, column chromatography, immunopurification methods, and other purification techniques. See, e.g., Scopes, *Protein Purification: Principles and Practice* (Springer-Verlag: New York (1982)), incorporated herein by reference.

As used herein, "immunoglobulin" refers to molecules which have specific immunoreactive activity. Antibodies are typically tetrameres of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad of immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (See, e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., "Immunology," (Benjamin, N.Y., 2nd ed. (1984)), and Hunkapiller and Hood, *Nature* 323:15–16 (1986), which are incorporated herein by reference). Single-chain antibodies, in which genes for a heavy chain and a light chain are combined into a single coding sequence, may also be used.

DETAILED DESCRIPTION OF THE INVENTION AND PREFERRED EMBODIMENT

ETS1 is a member of the ets gene family and is a cellular counterpart of the v-ets oncogene of the avian erythroblastosis virus, E26. The ETS1 gene is expressed at high levels in lymphoid cells, astrocytes and endothelial cells. The ETS1 protein is a nuclear phosphoprotein that binds to purine-rich DNA sequences and function as a transcription factor. The DNA-binding domain is localized at the carboxy-terminal region, and the transactivation domain is localized in the protein domain encoded by exons 5 and 6 of the ETS1 gene. The ETS1 protein-binding DNA sequences are present in the promoter regions of a number of housekeeping genes, as well as in certain other types of tissue-specific genes. The expression of the ETS1 gene is induced at late stages of thymocyte differentiation. In resting T-cells, the ETS1 gene is expressed at high levels and, upon activation of T-cells, the ETS1 gene products are decreased to low levels.

In addition to these properties and characteristic, it has now been discovered that the ETS1 gene possesses tumor suppressor activity, i.e., reduces tumorigenicity. More particularly, it has been found that introduction of the wild-type ETS1 gene into cells that do no endogenously express this gene results in tumor suppressive activity. Although tumor formation frequently results from multiple genetic alterations, expression of wild-type ETS1 can overcome these changes and suppress, i.e., reduce, tumorigenicity by either blocking the downstream targets for ETS2 gene products or, by inducing new gene products required for tumor suppression.

As such, in one aspect, the present invention provides a method for reducing cell tumorigenicity, the method comprising: transfecting a tumor cell with an ETS1 gene, the tumor cell not endogenously expressing this gene. In another aspect, the present invention provides a method for reducing cell tumorigenicity, the method comprising contacting a tumor cell with a peptide expressed by an ETS1 gene, the tumor cell not endogenously expressing this gene. The methods of the present invention are useful for reducing tumorigenicity both in vitro (i.e., in culture) and in vivo. As such, they can be used for both diagnostic and therapeutic purposes.

The ETS1 gene, i.e., the avian E26 erythroblastosis virus oncogene, homolog-1, has been deposited in the American Type Culture Collection (ATCC) at Rockville, Md. The deposits have been assigned the accession numbers: 61620 (human), 61621 (human) and 63131 (mouse). Access to the ETS1 gene can be obtained through the ATCC by reference to these accession numbers. The ATCC/NIH *Repository Catalogue of Human and Mouse DNA Probes and Libraries* (Seventh Edition, 1993)) describes the particulars with respect to these three ETS1 gene deposits. For a review of this gene and the techniques used in the isolation and cloning of this gene, see, for example, Watson, et al., *Proc. Natl. Acad. Sci. U.S.A.*, 82:7294–7298 (1985); and Watson, et al., *Proc. Natl. Acad. Sci. U.S.A.*, 83:1792–1796 (1986). Although the ETS1 gene is available through the ATCC, it will be readily apparent to those of ordinary skill in the art that this gene can be isolated and cloned from other sources using conventional techniques and procedures in the field of recombinant genetics. Two text books which describe in great detail the general methods of use in this invention are Sambrook, et al., *Molecular Cloning, A Laboratory Manual* (Cold Spring Harbor Publish., Cold Spring Harbor, N.Y. 2nd ed. (1989)), Methods in Enzymology, Vol. 152: *Guide to Molecular Cloning Techniques* (Berger and Kimmel (eds.), San Diego: Academic Press, Inc. (1987)) and Kriegler, *Gene Transfer and Expression: A Laboratory Manual* (W. H. Freeman, N.Y. (1990)), all of which are incorporated herein by reference.

Once the polynucleotide encoding the ETS1 protein is isolated and cloned, one may express the desired polypeptide in a recombinantly engineered cell such as bacteria, yeast, insect and mammalian cells. It is expected that those of ordinary skill in the art are knowledgeable in the numerous expression systems available for expression of the DNA encoding the ETS1 protein. No attempt to describe in detail the various methods known for the expression of proteins in prokaryotes or eukaryotes will be made.

In brief summary, the expression of natural or synthetic nucleic acids encoding the ETS1 polypeptide will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the ETS1 protein. To obtain high level expression of a cloned gene, it is desirable to construct expression plasmids which contain, at the minimum, a strong promoter to direct transcription, a ribosome binding site for transnational initiation, and a transcription/translation terminator. A more detailed description relating to the expression of the ETS1 protein in prokaryotes or eukaryotes is set forth hereinbelow.

1. Expression in Prokaryotes

Examples of regulatory regions suitable for this purpose in *E. coli* are the promoter and operator region of the *E. coli* tryptophan biosynthetic pathway as described by Yanofsky, *Bacteriol.* 158:1018–1024 (1984), and the leftward promoter of phage lambda (P$_L$) as described by Herskowitz and Hagen, *Ann. Rev. Genet.*, 14:399–445 (1980). The inclusion of selection markers in DNA vectors transformed in *E. coli* is also useful. Examples of such markers include genes specifying resistance to ampicillin, tetracycline, or chloramphenicol. See, Sambrook, et aL for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the ETS1 proteins are available using *E. coli, Bacillus sp.* and Salmonella (Palva, et al., *Gene* 22:229–235 (1983); Mosbach, et al., *Nature* 302:543–545 (1983). *E. coli* systems are presently preferred.

The ETS1 polypeptide produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. See, for example, U.S. Pat. No. 4,511,503.

When expressing the ETS1 protein in *S. typhimunium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium*, the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the ETS1 proteins is transformed into the his Salmonella strain. Integration of both the his sequences and a gene encoding a ETS1 protein occurs, resulting in recombinant strains which can be selected as $his^+$.

Detection of the expressed protein is achieved by methods known in the art and include, for example, radioimmunoassays, Western blotting techniques or immunoprecipitation. Purification from *E. coli* can be achieved following procedures described in U.S. Pat. No. 4,511,503.

2. Expression in Eukaryotes

Standard eukaryotic transfection methods are used to produce mammalian, yeast or insect cell lines which express large quantities of the ETS1 protein which is then purified using standard techniques. See, e.g., Colley, et al., *J. Biol. Chem.* 264:17619–17622 (1989), and "Guide to Protein Purification," in Vol. 182 of Methods in Enzymology (Deutscher (ed.), 1990), both of which are incorporated herein by reference.

Transformations of eukaryotic cells are performed according to standard techniques as described by Morrison, *J. Bact.* 132:349–351 (1977), or by Clark-Curtiss and Curtiss, *Methods in Enzymology* 101:347–362 (Wu, et. al., (eds.)), Academic Press, New York (1983).

Any of the well known procedures for introducing foreign nucleotide sequences into host cells can be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (See, Sambrook, et al., supra.). It is only necessary that the particular genetic engineering procedure utilized be capable of successfully introducing at least one gene into the host cell which is capable of expressing an ETS1 protein.

The particular eukaryotic expression vector used to transport the genetic information into the cell is not particularly critical. Any of the conventional vectors used for expression in eukaryotic cells can be used. Expression vectors containing regulatory elements from eukaryotic viruses are typically used. SV40 vectors include pSVT7 and pMT2. Vectors derived from bovine papilloma virus include pBV-1T , and vectors derived from Epstein Bar virus include pHEBO, and p205. Other exemplary vectors include pMSG, pAV009/$A^+$, pMTO10/$A^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually comprise selectable markers which result in gene amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with the ETS1 encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see, Sambrook, et al., supra., Ch. 16.

The prokaryotic elements that are typically included in the mammalian expression vector include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of the ETS1 protein in eukaryotic cells. A typical expression cassette contains a promoter operably linked to the DNA sequence encoding the ETS1 protein and signals required for efficient polyadenylation of the transcript. The DNA sequence encoding the ETS1 protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression* (Cold Spring Harbor Pres, Cold Spring Harbor, N.Y. 1983), which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

After the expression vector is introduced into the cells, the transfected cells are cultured under conditions favoring expression of the ETS1 protein which is recovered from the culture using standard techniques a. Expression in Yeast Synthesis of heterologous proteins in yeast is well known and described. *Methods in Yeast Genetics*, Sherman, et al., Cold Spring Harbor Laboratory (1982) is a well recognized work describing the various methods available to produce the ETS1 protein in yeast.

For high level expression of a gene in yeast, it is essential to connect the gene to a strong promoter system and to provide efficient transcription termination/polyadenylation sequences from a yeast gene. Examples of useful promoters include GAL1,10 (Johnson and Davies, Mol. and Cell. Biol., 4:1440–1448 (1984)) ADH2 (Russell, et al., *J. Biol Chem.*, 258:2674–2682, (1983)), PHO5 (EMBO J. 6:675–680, (1982)), and MFα1 (Herskowitz and Oshima, in *The Molecular Biology of the Yeast Saccharomyces*, (Strathern, Jones and Broach, eds.), Cold Spring Harbor Lab., Cold Spring Harbor, N.Y., pp.181–209, (1982)). A multicopy plasmid with a selective marker such as, for example, Leu-2, URA-3, Trp-1, and His-3 is also desirable.

The MFα1 promoter is preferred. The MFα1 promoter, in a host of the α mating-type is constitutive, but is switched off in diploids or cells with the a mating-type. It can, however, be regulated by raising or lowering the temperature in hosts which have a ts mutation at one of the SIR loci. The effect of such a mutation at 35° C. on an α type cell is to turn on the normally silent gene coding for the α mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz and Oshima, supra.).

The polyadenylation sequences are provided by the 3'-end sequences of any of the highly expressed genes, like ADH1, MFα1, or TPI (Alber and Kawasaki, *J. Mol. & Appl. Genet.*, 1:419–434(1982).

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., *Gene*, 8:17–24 (1979); Broach, et al., *Gene*, 8:121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs, *Nature* 275:104–109 (1978); and Hinnen, et al., *Proc. Natl. Acad. Sci. USA*, 75:1929–1933 (1978). The second procedure does not involve removal of the cell wall. Instead the cells are treated with lithium chloride or acetate and PEG and put on selective plates (Ito, et al., *J. Bact.* 153:163–168 (1983)).

Soluble ETS1 protein can be isolated from yeast by lysing the cells and applying standard protein isolation techniques to the lysates. The monitoring of the purification process can be accomplished by using Western blot techniques or other standard radioimmunoassays.

b. Expression in insect cells

The baculovirus expression vector utilizes the highly expressed and regulated *Autographa californica* nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding the ETS1 protein is inserted into a transfer plasmid vector in the proper orientation downstream from the polyhedrin promoter, and flanked on both ends with baculovirus sequences. Cultured insect cell, commonly *Spodoptera frugiperda*, are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plaque purification. The resulting recombinant virus, capable of expressing the ETS1 protein, is self-propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which the ETS1 gene can be inserted. For a summary of transfer vectors, see, Luckow and Summers, *Bio/Technology* 6:47–55 (1988). Preferred is the transfer vector pAcUW21 described by Bishop in *Seminars in Virology* 3:253–264 (1992).

c. Expression in Cell Cultures

ETS1 cDNA can be ligated to various expression vectors for use in transforming host cell cultures. The vectors typically contain gene sequences to initiate transcription and translation of the ETS1 gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of ETS1 protein. Mammalian cell systems often will be in the form of monolayers of cells although mammalian cell suspensions may also be used. Illustrative examples of mammalian cell lines include, for example, VERO and HeLa cells, Chinese hamster ovary (CHO) cell lines, WI38, BHK, COS-7 or MDCK cell lines.

As indicated above, the vector, i.e., a plasmid, which is used to transform the host cell, preferably contains DNA sequences to initiate transcription and sequences to control the translation of the ETS1 gene sequence. These sequences are referred to as expression control sequences. Illustrative expression control sequences are obtained from the SV-40 promoter (*Science* 222:524–527 (1983)), the CMV I.E. Promoter (*Proc. Natl. Acad. Sci. USA*. 81:659–663 (1984)) or the metallothionein promoter (*Nature* 296:39–42 (1982)). The cloning vector containing the expression control sequences is cleaved using restriction enzymes and adjusted in size as necessary or desirable and ligated with sequences encoding the ETS1 protein by means well known in the art. As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45:773–781 (1983)).

Additionally, gene sequences to control replication in the host cell may be incorporated into the vector such as those found in bovine papilloma virus type-vectors. See, e.g., Saveria-Campo, "Bovine Papilloma virus DNA a Eukaryotic Cloning Vector" in DNA Cloning, Vol. II, A Practical Approach (D. M. Glover, Ed., IRL Press, Arlington, Va., pp. 213–238 (1985)).

The transformed cells are cultured by means well known in the art. For example, as published in *Biochemical Methods in Cell Culture and Virology* (Kuchler, Dowden, Hutchinson and Ross, Inc. (1977)). The expressed ETS1 protein is isolated from cells grown as suspensions or as monolayers. The latter are recovered by well known mechanical, chemical or enzymatic means.

d. Expression Using A Retroviral Vector

Retroviral vectors are particularly useful for directing desired polynucleotides to the appropriate cells and for integration of the polynucleotides in the host cell genome (See, Friedman, "Progress Toward Human Gene Therapy," *Science*, 24:1275–1281(1989); Miller, A. D., *Human Gene Therapy* 1:15–19 (1990); Verma, I. M., *Scientific America* (November 1990); and Mulligan, R. C., *Science*, 260:926–931(1993), the teachings of which are incorporated herein by reference.) Briefly, a mammal having a tumor cell is inoculated with a cell line that produces a retroviral vector that contains the ETS1 gene. Typically, the cell line has been treated so that it replicates only for a short time, several days for example. Cells so treated are referred to as "mortalized."Irradiation, for example, is a convenient mortalization treatment. Thus, although the cell line has been mortalized, it is capable of producing the engineered retrovirus for about 4 to 8 days. The defective-retrovirus can invade and transfect cells, but it cannot undergo further virus production. The mortalized cells carry the retrovirus which serves as a vehicle for carrying a gene of interest into the cell, e.g., a tumor cell.

More particularly, replication-defective retroviral vectors are produced when a defective DNA viral genome is introduced into a packaging cell line. The defective genome contains the sequences required for integration into the target cell genome, for packaging of the genome into infectious virions, as well as those viral sequences required for expression of the therapeutic gene or other polynucleotide contained within the defective viral genome. The packaging cells comprise the gag, pol, and env genes which encode the viral core and envelope components. These core and envelope proteins assemble around the defective genome, thus producing retroviral vectors.

A number of standard techniques are used to ensure safety of retroviral vectors. For instance, the defective genome is introduced into the cell separately from the genes encoding the core and envelope components. In this way, recombination between the genome and the core and envelope genes, which would lead to the packaging of complete viral genomes, is extremely unlikely. The resulting virions should therefore not comprise the gag, pol, and env genes and are thus replication-defective. Homologous recombination, however, between the inserts can lead to the production of infectious virions. Typically, the packaging cells are produced by introducing the gag, pol, and env genes on at least two separate plasmids. This scheme effectively prevents homologous recombination leading to reconstruction of infectious virus because the probability of multiple, independent homologous recombination events occurring is extremely low.

Retroviral vectors can also be designed to prevent synthesis of viral proteins by the integrated defective genome. For instance, if a portion of the gag gene is included to increase packaging efficiency, a stop codon can be introduced into the gene to prevent synthesis of gag proteins. Miller, et al., *BioTechniques*, 7:982-988 (1989), which is incorporated herein by reference.

e. Expression Using Direct Gene Transfer

In addition to the foregoing methods, the ETS1 gene can be directly introduced into the cells or tissue of interest using techniques known to those of skill in the art. The ETS1 gene can, for example, be directly introduced into the cells or tissue of interest using a DNA-liposome complex. Plasmid ETS1 DNA complexed to liposomes can be used to transfer genes by injection or catheter into cells or tissue where they stimulate localized biological responses. Briefly, the expression vector plasmid is produced using the procedures and techniques described supra. Once the plasmid is grown and purified, the plasmid-liposome complex is formed by, for example, incubating the plasmid in lactated Ringer's solution (see, infra, for a detailed discussion regarding liposomes). The DNA-liposome complex is subsequently introduced into the cells or tissue of interest by injection or catheter. For a detailed review of the use of this technique, see, e.g., Nabel, et al., *Proc. Natl. Acad. Sci. USA*, 90:11307-11311 (1993) and the references cited therein, the teachings of which are hereby incorporated by reference.

It will be readily apparent to those of ordinary skill in the art that as modifications and improvements are made to the previously described techniques for expressing the ETS1 gene, they can be incorporated into the methods of the present invention. Moreover, it will be readily apparent to those of ordinary skill in the art that in the method comprising contacting the tumor cell with the protein or, interchangeably, peptide expressed by the ETS1 gene, the protein or peptide is expressed using the techniques described above and, isolated and purified using conventional techniques known to and used by those of in the art. Alternatively, the protein or peptide can be prepared using chemical peptide synthesis techniques known to those of in the art, including both solution methods and solid phase methods. Techniques for solid phase synthesis are described by Barany and Merrifield, *Solid-Phase Peptide Synthesis*, in *The Peptides: Analysis, Synthesis, Biology* (Gross and Meienhofer (eds.), Academic press, N.Y., vol. 2, pp. 3-284 (1980)); Merrifield, et al., *J. Am. Chem. Soc.* 85, 2149-2156 (1963); and Stewart, et al., *Solid Phase Peptide Synthesis* (2nd ed., Pierce Chem. Co., Rockford, Ill. (1984)), the teachings of which are hereby incorporated by reference.

It has been determined that the methods of the present invention are useful for reducing tumorigenicity in cells that do not endogenously express the ETS1 gene. More particularly, it has been found that the methods of the present invention are particularly useful for reducing tumorigenicity in epithelial cells as these cells do not express ETS1 endogenously. A cell is said "not to endogenously express the ETS1 gene" if the ETS1 mRNA present in the cell represents less than 0.002% of the total mRNA. Moreover, the term "epithelial cell" is used herein to refer to the epithelium, i.e., the covering of internal and external surfaces of the body, including the lining of vessels and the small cavities. These cells are present in the colon, breast, ovarian, prostate, kidneys, etc. As such, the methods of the present invention are useful for reducing tumorigenicity in cells that do not endogenously express the ETS1 gene and, in particular, for reducing tumorigenicity in colon, breast, ovarian, prostate and hepatic epithelial tumor cells.

A variety of methods can be used to determine whether or not a given cell endogenously expresses the ETS1 gene. A number of DNA and RNA measurement techniques using, for example, nucleic acid hybridization are known to those of skill in the art. See, e.g., Sambrook, et al., supra. and Berger and Kimmel, (1987), supra. Moreover, the teachings of Suzuki, et al. (*Int. J. Oncol*, 3:565-573 (1993)) provide PCR primers, nucleic acid probes, hybridization conditions and other techniques which are useful for determining whether or not the ETS1 gene or the expression product of the ETS1 gene is present in a given cell.

One method for evaluating the presence or absence of ETS1 DNA in a sample involves a Southern transfer. Briefly, the digested genomic DNA is run on agarose slab gels in buffer and transferred to membranes. Hybridization is carried out using probes as described above. Visualization of the hybridized portions allows the qualitative determination of the presence or absence of the ETS1 gene. Similarly, a Northern transfer may be used for the detection of ETS1 mRNA in samples of RNA. In brief, the mRNA is isolated from a given cell sample (e.g., colon cells) using an SDS-phenol or acid guanidinium-phenol-chloroform extraction method. The MRNA is then electrophoresed to separate the mRNA species and the mRNA is transferred from the gel to a nitrocellulose membrane. As with the Southern blots, labeled probes are used to identify the presence or absence of a ETS1 transcript.

A variety of nucleic acid hybridization formats are known to those skilled in the art. For example, common formats include sandwich assays and competition or displacement assays. Hybridization techniques are generally described in Berger and Kimmel, (1987), supra.; "*Nucleic Acid Hybridization, A Practical Approach*" (Hames, B. D. and Higgins, S. J. (eds.), IRL Press, 1985; Gall and Pardue, (*Proc. Natl. Acad. Sci., U.S.A.* 63:378-383 (1969)); and John, Burnsteil and Jones (*Nature*, 223:582-587 (1969)). Moreover, the sensitivity of the hybridization assays may be enhanced through the use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q-Beta Replicase systems.

An alternative means for determining the level of expression of the ETS1 gene is in situ hybridization. In an in situ hybridization assay cells are fixed to a solid support, typically a glass slide. If DNA is to be probed, the cells are denatured with heat or alkali. The cells are then contacted with a hybridization solution at a moderate temperature to permit annealing of ETS1 specific probes that are labelled. The probes are preferably labelled with radioisotopes or fluorescent reporters. In situ hybridization assays are well known and are generally described in Angerer, et al. (*Methods Enzymol.* 152:649–660 (1987)).

In addition to the detection of the ETS1 gene or the ETS1 gene expression product using nucleic acid hybridization technology, one can use immunoassays to detect either the product of the ETS1 gene or the presence of antibodies to the product of the ETS1 gene. Immunoassays can be used to qualitatively or quantitatively analyze the ETS1 protein or ETS1 antibodies. A general overview of the applicable technology can be found in Harlow and Lane, *Antibodies: A Laboratory Manual* (Cold Spring Harbor Pubs., N.Y. (1988)), incorporated herein by reference.

Although those of ordinary skill will be able to raise antibodies which are specifically reactive with the ETS1 antigens, such antibodies are commercially available and or readily preparable using the teachings in the art. For example, the human ETS1 (K17C) antisera and the cognate peptide can be purchased from Cambridge BioResearch Chemicals. The pan ets monoclonal antibody (mAb) and the cognate peptide have been previously described by Bhat and Papas, Hybridoma, 11:277–294 (1992). These monoclonal or polyclonal antibodies specific for the ETS1 gene product can be used in various immunoassays including, for example, ELISA, competitive immunoassays, radioimmunoassays, Western blots, indirect immunofluorescent assays and the like.

The methods of the present invention further include observing for a reduction in tumorigenicity, i.e., tumorigenic potential, of the sample tumor cells. This step includes observing for an inhibition of or reduction in sample tumor cell growth. Measures of tumor cell growth that are suitable include, for example, growth rate, colony formation in soft agar, tumorigenicity in an experimental animal, tumor cell phenotype, thymidine incorporation, and drug sensitivity. All of these are factors which alone or in combination with one another can be used to determine whether or not cell tumorigenicity has been reduced. A "reduction in tumorigenicity" is said to have occurred when, for example, a reduction, i.e., inhibition, in growth rate, colony formation in soft agar, tumor size, thymidine incorporation, etc. is observed. Additionally, it will be readily apparent to those of ordinary skill in the art that tumor phenotype(s), as noted by the clinician or other qualified observer, can be used to determine whether there has been a reduction in cell tumorigenicity. Observation for inhibition of growth is usually made daily, although other time intervals are practiced.

The growth rate, for example, can be measured by macroscopically observing how rapidly the tumor cells grow. This may be expressed as a doubling time (the amount of time it takes for the cells to double their numbers). Tumor cell growth rate can be measured in tissue culture by adding a fixed number of cells in tissue culture medium to a flask, culturing them in a 5% $CO_2$ humidified atmosphere, removing and counting an aliquot of the cells at different time points. By plotting the cell counts over time, it is possible to determine the doubling rate of the tumor cells.

Colony formation in soft agar is another measure of tumor growth. See, Wu, Y. and D. Cai, *Proc. Soc. Exp. Biol. Med.*, 201(3):284–288 (1992).

Tumorigenicity in an experimental animal can be measured by injecting an aliquot of cells, such as approximately $10^6$ cells, into an experimental animal subcutaneously and observing for tumor formation. See, Yeung, et al., *J. Surg. Res.* 53(2):203–210 (1992).

Phenotype refers to how the tumor looks, typically microscopically, but gross or macroscopic appearance can be observed. The phenotype changes depending on the growth rate of the tumor cells. For instance, the microscopic morphology of cells that are rapidly dividing and growing is different than that of cells that are dividing and growing at a normal rate. Determination of tumor cell phenotype is well within the ability of one with ordinary skill in the art.

Thymidine incorporation can be a measure of tumor cell growth because thymidine is incorporated into rapidly growing cells at a higher rate than into static or less rapidly growing cells. See, Saito, et al., *Eur. Arch. Otorhinolaryngol*, 249(7):400–403 (1992); and Brooks, D. J. and Carewal, H. S., Int. *J. Clin. Lab. Res.*, 22(4):196–200 (1992).

It will be readily apparent to those of ordinary skill in the art that a reduction or improvement in any one of the foregoing factors establishes that there has been a reduction in cell tumorigenicity.

As previously mentioned, the present invention provides a method for reducing cell tumorigenicity, the method comprising contacting a tumor cell with a peptide expressed by an ETS1 gene, the tumor cell not endogenously expressing this gene. It will be readily apparent to those of ordinary skill in the art that in addition to the entire peptide, biologically active fragments of the peptide may be used to reduce cell tumorigenicity. If biologically active fragments of the ETS1 peptide are used, it will be readily apparent to those of ordinary skill in the art that only that portion of the ETS1 gene encoding the biologically active fragment need be expressed if recombinant techniques are used to make the peptide. The selection of the portion of the ETS1 gene required to express a given peptide fragment will be apparent to those of ordinary skill in the art.

As such, the native ETS1 peptide may be subject to various changes, such as insertions, deletions, and substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the native ETS1 peptide can be identified by single amino acid substitutions, deletions, or insertions using conventional techniques known to those of skill in the art. In addition, the contributions made by the side chains of the residues can be probed via a systematic scan with a specified amino acid (e.g., Ala).

Moreover, peptides which tolerate substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the ETS1 peptide.

Structure function analysis of the ETS1 proteins has shown that the minimal DNA-binding domain consists of 85 amino acid residues and is localized at the carboxyl-terminal region (Wang, et al., *J. Exp. Med.*, 175:1391 (1992). It has also been found that the transactivation domain maps to the protein domain encoded by exons 5 and 6 of the ETS1 gene (Schneikert, et al., *Oncogene*, 7:249 (1992)), a region not well conserved among other members of the ets family of genes. Exon 6 of human ETS1 encodes a region that spans from amino acid residues 177 to 243; this region has been found to be important with respect to reducing cell tumorigenicity. Thus, a biologically active peptide fragment can comprise, for example, amino acids residues 177 through 243. In addition, this peptide fragment can be shorten and modified further without loss of biological activity. Moreover, within this region, it has been determined, through an analysis of the mutant form of the ETS1 peptide, that replacement of acidic amino acids 202 and 212 of the native ETS1 peptide with neutral or slightly basic amino acid residues results in the peptide's inability to reduce tumorigenicity. Thus, to be biologically active, the peptide fragment should contain amino acids 202 and 212 of the native ETS1 amino acid sequence. If these two amino acids are, in fact, modified, they should be modified with like, i.e., functionally equivalent, amino acid residues. Those of ordinary skill in the art will readily be able to carry out the routine experimentation necessary to determine which amino acids can be substituted, modified or deleted without loss in the biological activity of the ETS1 peptide, i.e., without loss in the ability of the ETS1 peptide to reduce or inhibit cell tumorigenicity.

In conjunction with this aspect, the present invention provides pharmaceutical compositions comprising the ETS1 protein or a fragment thereof in an amount sufficient to reduce or inhibit tumorigenicity, and a pharmaceutically acceptable diluent, carrier or excipient. The pharmaceutical compositions of the present invention are suitable for use in a variety of drug delivery systems. Suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527–1533 (1990), which is incorporated herein by reference.

As described above, the ETS1 gene and the expression product of the ETS1 gene have tumor suppressor activity. As such, the present invention provides for therapeutic compositions or medicaments comprising one of the ETS1 peptide of, fragments thereof as described hereinabove in combination with a pharmaceutically acceptable excipient, wherein the amount of the ETS1 peptide present in the composition is sufficient to provide a therapeutic effect.

In a therapeutic application, the ETS1 peptide is embodied in pharmaceutical compositions intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the ETS1 peptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the ETS1 peptide is preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the ETS1 peptide of the invention are administered to a patient in an amount sufficient to reduce, i.e., inhibit, cell tumorigenicity. An amount adequate to accomplish this is defined as "therapeutically effective dose." Amounts effective for this use will depend on, for example, the peptide composition employed (e.g., whether the ETS1 peptide or a fragment thereof is used), the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring or observing the various factors described above for determining whether a reduction in tumorigenicity has been achieved.

The ETS1 peptides useful in the methods or compositions of the present invention may also be administered via liposomes, which serve to target the peptides to a particular tissue, such as lymphoid or colon tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/ immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, for example, Szoka, et al., *Ann. Rev. Biophys. Bioeng.*, 9:467 (1980); U.S. Pat. Nos. 4,235,871, 4,501,728, 4,837,028; and 5,019,369, the teachings of which are incorporated herein by reference.

For targeting to the immune cells, a ligand to be incorporated into the liposome can include, for example, antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

The invention will now be described in greater detail by way of specific examples. The following examples are offered for illustrative purposes, and are intended neither to limit the invention in any manner.

EXAMPLES

A. Construction Of Expression Vectors That Express EST1. i.e., p51 and Other Experimental Protocols The 1.9 kb HindIII fragment containing full length human ETS1 cDNA was subcloned into HindIII site of pcDM7 (Ho, et al., *Science*, 250: 814–819 (1990)) and pcDNA (Invitrogen) eukaryotic expression vectors. The recombinant plasmid DNA containing full length plasmid DNA was isolated by alkaline lysis and CsCl gradient centrifugation. A 15 μg of ETS1 expression plasmid DNA and 1 μg of pSV2 neoplasmid DNA (G418 selectable marker) were suspended in 50 μg of lipofection reagent and added to DLD-1 cells in 60 mm plates containing 3 ml of serum-free RPMI 1540 medium. After 8 hours of incubation, at 37° C., 3ml of RPMI 1640 medium supplemented with 30% fetal calf serum was added and incubation was continued for 24 hours. Cells were removed from dishes by trypsinization, and split into three 60 mm dishes and maintained in RPMI 1640 medium containing 15% fetal calf serum and 400 μg/ml of G418 solution. Cells were watched on a daily basis for appearance of colonies. After two to three weeks, independent colonies were picked and expanded further and maintained in G418 medium as described above. Transfectants were further characterized for ETS1 cDNA and RNA by Southern and Northern blot analyses using 1.9 kb HindIII fragment containing full length ETS1 cDNA described before (Bhat, et al., *Proc. Natl. Acad. Sci. USA*, 84:3161 (1987)). The levels of ETS1 proteins were further quantified in positive transfectants by radio-immune precipitation analyses from $^{35}S$ Methionine labelled cell lysate using well characterized ETS1 specific antibodies (Koizumi, et al., *Oncogene*, 5:675 (1990)).

Five independent cell lines expressing ETS1 at different levels along with neotransfectants were further characterized for their ability to form colonies on soft agar. 1×10⁴ cells were seeded in 0.33% noble agar (DIFCO) in RPMI 1640 with 15% fetal calf serum. After 10 days of incubation, to identify colony size and efficiency of cell growth, cells were stained overnight with p-iodonitro-tetrazolium violet (1.0 mg/ml) dye solution; colonies were counted. The tumorigenic potential of the ETS1 transfectants in nude mice were studied by injection 2×10⁶ cells subcutaneously into the right anterior flank area of 6 to 8 week old female nude mice. These mice were observed for the appearance of tumor growth. After 4 weeks animals were exsanguinated and tumor size was measured and samples were sent for biochemical and histopathological studies.

B. Analysis Of EST1 Gene Expression In Vector Transduced Cell Lines

To identify if the products of the ETS1 gene have any tumor-suppressive activity, the effects of this gene in colon cancer cells were examined because an established and well-characterized cell line from a patient's tumor sample is available for easy manipulation (Dexter, et al., *Cancer Res.*, 39:1020 (1979)). These cells are able to form tumors in nude mice, and they express very low levels of ETS1, but abundant levels of ETS2 gene products (Suzuki, et al., *Int. J. Oncol*, 3:565–573 (1993)). [In DLD-1 cells, high levels of ETS2 mRNA and proteins were detected by RNS blot analysis and radioimmunoprecipitation using ETS2 specific U244 mAb.] The full-length ETS1 protein was expressed in DLD-1 and HCT1 16 cells under the control of cytomegalovirus (CMV) promoter. [Two ETS1 expression vectors, pcDM7-ETS1 (11, 20) and pcDNAI-ETS1 contain full-length ETS1 cDNA cloned in HindIII site of pcDM7 and pcDNA1 (Invitrogen), respectively. Human ETS1 cDNA expression vectors were co-transfected with pSV2-neo into DLD-1 cells using lipofectin reagent (BRL) followed by selection with G418 (400 μg/ml).] Several independent cell-lines capable of expressing ETS1 at different levels were obtained and chosen for further examination. The DLD-1 cell-lines 1-1, 1-7 and 3-2 were transfected with pcDM7-ETS1, and the DLD-1 cell-lines 2-3, 2-4 and 2-8 were transfected with pcDNAI-ETS1. The cell lines neo-1, 2 and 3 were transfected with pSV2neo plasmid alone; these served as controls. DNA blot analyses of the six cell-lines showed a characteristic 1.9-kb ETS1 HindIII fragment and a different size ApaL-1 fragment confirming that these transfectants truly represent independent clones.

The levels of exogenous ETS1 mRNA and proteins were examined in these cells by RNA blot analysis and radioimmunoprecipitation using the well-characterized E44 monoclonal antibody (mAb) recognizing the ETS1 proteins (Koizumi, et al., supra, (1990)). It has previously been shown that human T-lymphoma cells express 51 and 42 kDa proteins derived from full-length and alternatively-spliced mRNA lacking exon 7, respectively (S. Koizumi, et al., supra (1990); R. Fisher, et al., *J. Biol. Chem.*, 267:17957 (1992)). However, only the 51 kDa ETS1 protein (i.e., p51) was expected to be translated from the exogenously expressed full-length cDNA. In DLD-1 transfectants, except for the DLD-2-3 cells, the p51 is the only ETS1 protein expressed at different levels. It is known that p51 is encoded by exogenous ETS1 because (i) it is undetectable in parental cells as well as in cells transfected with pSV2-neo alone, (ii) it is immunoprecipitated by two different ETS1 antibodies and competed by cognate peptides (Bhat, et al., *Hybridoma*, in press (1994)), (iii) the levels of p51 correlated well with the levels of ETS1 mRNA initiated from the CMV promoter and (iv) the p51 has a size similar to the endogenous full-length proteins detected in T-lymphoma cells. Also, it has previously been shown that the exogenous ETS1 protein expressed in DLD-1-7 cells is localized in the nucleus and it binds to the purine-rich DNA sequences. Moreover, this product has similar biochemical properties to the ETS1 protein expressed in lymphoid cells (Suzuki, et al., supra (1993)).

2-8 cells that express higher levels of ETS-1 protein; this observation is consistent with the longer doubling time exhibited by the DLD-3-2 cells.

TABLE 1

GROWTH AND TUMORIGENICITY OF THE ETS-1 TRANSFECTANTS

| Cell Line | ETS-1 Expression | Tumor Incidence in Nude Mice* 2W | 3W | 4W | Tumor Diameter† (in mm, 4W) | Doubling Time** | Soft Agar Colony‡ |
|---|---|---|---|---|---|---|---|
| DLD-1: | | | | | | | |
| DLD-1 | — | 3/3 | 3/3 | 3/3 | 13.2 | 21.5 | 30.5 |
| DLD-1 neo-1 | — | 5/6 | 5/6 | 6/6 | 9.4 | 19.0 | 20.9 |
| DLD-1 neo-2 | — | 5/6 | 5/6 | 5/6 | 10.0 | 18.0 | 24.0 |
| DLD-1 neo-3 | — | 4/5 | 5/5 | 5/5 | 11.0 | 24.2 | ND |
| DLD-1 ETS-1 transfectants Wild-Type: | | | | | | | |
| 1-1 | + | 5/7 | 7/7 | 6/7 | 12.8 | 22.0 | 13.2 |
| 2-4 | + | 2/5 | 3/5 | 5/5 | 5.3 | 24.5 | 17.5 |
| 3-2 | ++ | 2/6 | 4/6 | 4/6 | 4.4 | 39.0 | 3.4 |
| 2-8 | +++ | 0/4 | 1/4 | 2/4 | 3.8 | 21.0 | 10.4 |
| 1-7 | +++++ | 0/9 | 0/9 | 3/9 | 3.7 | 19.5 | 7.4 |
| Wild-Type & Mutant: | ++++*** | 1/5 | 3/5 | 4/5 | 7.1 | 23.2 | 31.4 |
| 2-3 Mutant: | | | | | | | |
| M-1 | ++ | 3/5 | 3/5 | 4/5 | 5.8 | ND | ND |
| M-9 | ++ | 4/5 | 4/5 | 5/5 | 8.0 | ND | ND |
| M-12 | + | 5/5 | 5/5 | 5/5 | 10.4 | ND | ND |
| M-13 | +++ | | | | | | |
| M-21 | +++ | | | | | | |
| M-26 | + | 5/5 | 5/5 | 5/5 | 10.6 | ND | ND |
| M-27 | + | 5/5 | 5/5 | 5/5 | 7.1 | ND | |

*Cells ($2 \times 10^6$) of each cell line were injected subcutaneously into the right anterior flank area of the 6–8-week-old female nude mice.
**Cells were plated at $2 \times 10^5$ in RPMI-1640 medium containing 15% FCS.
***Wild-type and mutant ETS-1 are expressed at similar levels.
†The size of tumors is expressed as the mean diameter of the tumors in nude mice 4 weeks after the injection day.
‡Number of soft agar colonies/$1 \times 10^4$ cells plated. Scored after 10 days' incubation.
W = week; ND = Not done; —, ETS1 mRNA and proteins are not detectable; + to +++++ relatively low to high levels of ETS1 mRNA and proteins, respectively, among DLD-1 ETS1 transfectants.

To determine whether overexpression of ETS1 has any effect on cell proliferation, the growth properties of the DLD-1 transfectants expressing different levels of ETS1 proteins were studied. No substantial differences in their growth rates (Table 1) were observed, suggesting that the ETS1 expression did not affect the anchorage-dependent growth rates of the DLD-1 cells. On the other hand, anchorage-independent growth rates, indicated by the colony-forming ability in soft agar, were reduced in the ETS-1 transfectants. The ability to form colonies in soft agar was dependent on the level of wild-type ETS1 expression (See, Table 1). Not only the efficiencies, but also the sizes of soft agar colonies, were suppressed by transfection of ETS1, i.e., cells expressing higher levels of ETS1 showed a reduction in the number of colonies in soft agar, as well as in their colony size. The reduction in soft agar colony number was noticeable only if ETS1 expression occurred at moderate levels, suggesting that the ETS1 product(s) may be titrating out other gene products which are involved in anchorage-independent growth. The DLD-3-2 cells showed less colony-forming ability in soft agar compared with the DLD- C. In Vivo Inhibition Of Tumor Formation In Mice Since tumor formation of cells in vivo correlates well with their colony-forming ability in soft agar, the tumorigenic potential of the ETS1 transfectants in nude mice was investigated. The parental and neo transfectants (i.e., controls) all formed tumors in nude mice within three weeks. In contrast, DLD-1-7 cells expressing high levels of the ETS1 protein, produced no tumors in all nine nude mice studied within the same incubation times (Table 1). Three other ETS1 transfectants (i.e., DLD-2-8; 3-2, 2-4) also showed reduced tumor incidences, but at different levels. Thus, like soft agar colony formation, the nude mice tumorigenicity assay appeared to be dependent on the levels of ETS1 gene expression.

The escape from suppression of tumorigenicity could be accompanied by changes in the levels of ETS1 gene expression. Since small tumors arose after four weeks in nude mice injected with the DLD-1-7 and 2-8 cells expressing the abundant wild-type p51, these tumors were characterized for aberrant changes in histology and to determine the levels of ETS1 protein. No significant differences were found in histological examinations between the tumors of the ETS1 transfectants and those of control cells. On the other hand, protein samples obtained from tumor initiated by DLD-1-7 and 2-8 cells, showed a reduced amount of the ETS1 protein than the cells originally used for inoculation. Since higher tumor incidence was obtained in DLD-1 transfectants expressing lower levels of ETS1 protein, it is possible that the subpopulation of DLD-1-7 and 2-8 cells expressing these low levels of ETS1 proteins were being selected in vivo and thus, formed tumors at a higher incidence in nude mice. These results further confirm the observation that the cells expressing the lower levels of ETS1 proteins had a higher tumorigenic potential in vivo.

D. Characterization of the Mutated Form of the EST1 Protein

One of the DLD-1 transfectants, DLD-2-3, expressing ETS1 proteins showed no reduction in colony-forming ability and tumorigenicity (compared to control calls), in spite of abundant expression of ETS1 proteins (See, Table 1). Careful analysis of ETS1 proteins revealed that in this cell line, in addition to p5 1, another faster migrating 50 kDa protein (i.e., p50) was specifically recognized by three different ETS1 antibodies raised against the amino, middle and carboxy-terminal regions of ETS1 proteins (S. Koizumi, et al., supra (1990)) in both radioimmunoprecipitation and Western blot analysis. Both 50 and 51 kDa ETS1 are expressed at similar levels, share at least four different ETS1 epitopes in common and are derived from transfected ETS1 cDNA. Expression of p50 ETS1 appears to block the reduction of tumorigenicity rendered by p51 ETS1. Therefore, the p50 protein was further characterized. As described above, p50 was recognized by three different ETS1 antibodies raised against oligopeptides derived from epitope regions encoded by exons 6 (αE44), 7 (αK17C), 8 and 9 (αpan-ets) of the human ETS1 protein. [The synthesized peptide corresponding to E44-eptiope mapped in exon 6 of ETS1 (N. K. Bhat, et al., *Hybridoma*, in press (1994)) was used for competition experiments. These results were confirmed by another ETS1 antibody, K17C (Cambridge Research Chemicals), recognizing exon 7 of ETS1 and the cognate peptide (Suzuki, et al., Intl. J. Oncol., 3:565-573 (1993)); Bhat and Papas, *Hybridoma*, 11:277 (1992).] The G19E monoclonal antibody raised against the last 19 carboxy-terminal amino acids of ETS1 (Gly$^{422}$ to Glu$^{441}$) also recognized the p50, indicating that the observed change in the gel-mobility is not due to truncation of the protein, but rather it appears to be due to some other mutation(s) in the EST1 protein.

To characterize the mutation, the ETS1 cDNA clone was isolated from genomic DNA from DLD-2-3 cells using a polymerase chain reaction and subcloned using a PCRII vector (Invitrogen). The cDNA clones were characterized according to the size of the ETS1 protein produced using an in vitro transcription-coupled translation system. The size of the protein immunoprecipitated from the in vitro translation product generated from 0-15 cDNA, is very similar to the faster migrating p50 ETS1 protein seen in DLD-2-3 cell extracts, suggesting that the cDNA 0-15 encodes the p50 ETSI protein. The DNA sequence analyses of clone 0-15 (i. e., clone 0-15, subcloned into pCRII plasmid, was used as a template for determination of nucleotide using the sequence rapid well DNA sequencing kit (USB), following the manufacturer's protocol) revealed that it is homologous to ETS1 (100%), except for four nucleotide substitutions (at codons: 202; 208; 212; 296) in its entire open reading frame. Two substitutions in codons 208 (GTC to GTT) and 296 (CCC to CCT) did not effect any change in its amino acid residues. However, substitutions in codons 202 (GAG to GGG) and 212 (GAC to CAC) did change Glu$^{202}$ to Gly$^{202}$ and Asp$^{212}$ to His$^{212}$, respectively (See, Table 2). Substitution of acidic by neutral or slightly basic amino acid residues could account for the observed faster migration of this p50 mutant ETS1 protein, similar to the mutation (Glu$^5$ to Val$^6$) that occurred in sickle cell hemoglobin (V. Ingram, Nature, 180:326 (1957)).

TABLE 2

MUTATIONS FOUND IN p50 ETS-1 cDNA 0-15)

| Codon | Mutation Nucleotide* | Amino Acid |
|---|---|---|
| 202 | GAG→GGG | Glu→Gly |
| 212 | GAC→CAC | Asp→His |
| 208 | GTC→GTT | Val→Val |
| 296 | CCC→CCT | Pro→Pro |

*Mutations were confirmed on both strands.

Structure function analysis of the ETS1 proteins have shown that the minimal DNA-binding domain consists of 85 amino acid residues and is localized at the carboxyl-terminal region (C. Wang, et al., *J. Exp. Med.*, 175:1391 (1992)). The transactivation domain maps to the protein domain encoded by exons 5 and 6 of the ETS1 gene (J. Schneikert, et al., *Oncogene*, 7:249 (1992), a region not well conserved among other members of the ets family of genes. Exon 6 of human ETSI encodes a region that spans from amino acid residues 177 to 243 (Jorcyk, et al., *Oncogene*, 6:523 (1991)); therefore, the mutations observed in p50 appear to be clustered around the putative transactivation domain of ETS1. To find out if the mutant ETS1 has any transcriptional activities, the ability of mutant ETS1 proteins to transactivate the ets binding sequence (EBS) containing reporter constructs was examined. It was found that mutant (p50) ETS1 is not able to transactivate CAT gene expression through EBS, while wild-type ETS1 (i.e., p5 1) transactivated the EBS CAT by 2- to 3-fold. The failure to transactivate EBS CAT gene expression by mutant ETS1 is not due to transfection efficiency or expression of p50 ETS1, because similar levels of p50 and p51 are expressed in DLD-1 cells. Moreover, to find out if the mutant ETS1 protein is capable of binding to DNA, its ability to bind to the ets binding DNA sequences (EBS) by the electrophoretic mobility shift assay using proteins made in vitro in reticulocyte lysates was tested. It was found that both mutant and wild-type ETS1 are equally capable of binding to DNA. These results are consistent with the finding that there is no amino acid substitution in the DNA binding domain, and the mutation in the putative transactivation domain affects the transcriptional activation. To find out if mutant ETS1 also has lost its ability to reduce tumorigenicity, the mutant ETS1 protein was expressed, under the control of the CMV promotor, into DLD-1 cells and several independent transfectants expressing different amounts of protein were obtained. M-1 and M-9 express higher levels of mutant ETS1 compared to wild-type ETS1 expressed in DLD-1-2-8 transfectants. The tumorigenic potential of these mutants in nude mice and found that both M-1 and M-9 transfectants were more tumorigenic than 2-8 transfectants. These results further confirm that the reduction in tumorigenicity is due to overexpression of wild-type ETS1 in these colon cancer cells.

To further confirm that the ETS1 when overexpressed in colon cancer cells, reduces tumorigenicity, the effect of wild-type and mutant ETS1 in another colon cancer cell line, HCT116, were examined. Both wild-type and mutant forms of ETS1 under the control of the CMV promoter were expressed, and independent clones expressing different amounts of ETS1 protein were obtained. As shown in Table 1, only wild-type, but not mutant, ETS1 protein is capable of reducing the tumorigenicity. These results, taken together, indicate that the ETS1 proteins may be able to regulate tumor suppression, either by activating gene products necessary for tumor suppression, or by inactivating or titrating out gene products involved in anchorage-independent growth.

All of the foregoing references are hereby incorporated in their entirety by reference.

The foregoing description and the following examples are offered primarily for purposes of illustration. It will be readily apparent to those skilled in the art that the operating conditions, materials, procedural steps and other parameters of the system described herein may be further modified or substituted in various ways without departing from the spirit and scope of the invention. Thus the invention is not limited by the description and examples, but rather by the appended claims.

What is claimed is:

1. A method for reducing cell tumorigenicity of a cell, said method comprising:
   contacting a tumor cell with a peptide expressed by an ETS1 gene, said tumor cell not endogenously expressing said ETS1 gene.

2. A method in accordance with claim 1 further comprising the step of observing for a reduction in tumorigenicity of said tumor cells.

3. A method in accordance with claim 1 wherein said tumor cell is an epithelial cell.

4. A method in accordance with claim 3 wherein said epithelial cell is selected from the group consisting of colon, breast, ovarian, prostate and hepatic cells.

5. A method in accordance with claim 3 wherein said epithelial cell is a colon cell.

6. A method in accordance with claim 1 wherein said polypeptide includes amino acids 202 and 212 of the native ETS1 amino acid sequence.

* * * * *